United States Patent
Amberg et al.

(10) Patent No.: US 9,375,190 B2
(45) Date of Patent: Jun. 28, 2016

(54) RADIOGRAPHY DEVICE AND METHOD FOR EXAMINATIONS IN THE FIELD OF PEDIATRIC RADIOLOGY

(71) Applicant: SIEMENS AKTIENGESELLSCHAFT, Munich (DE)

(72) Inventors: Jessica Amberg, Bubenreuth (DE); Hayo Knoop, Forchheim (DE); Gudrun Roth-Ganter, Ratshausen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 145 days.

(21) Appl. No.: 14/227,082

(22) Filed: Mar. 27, 2014

(65) Prior Publication Data

US 2014/0294155 A1    Oct. 2, 2014

(30) Foreign Application Priority Data

Mar. 27, 2013    (DE) .................. 10 2013 205 499

(51) Int. Cl.
*A61B 6/00*    (2006.01)

(52) U.S. Cl.
CPC ............... *A61B 6/4452* (2013.01); *A61B 6/488* (2013.01); *A61B 6/542* (2013.01); *A61B 6/545* (2013.01); *A61B 6/588* (2013.01)

(58) Field of Classification Search
CPC .................. G01N 23/04; G01N 2223/1016
See application file for complete search history.

(56) References Cited

U.S. PATENT DOCUMENTS

| | | |
|---|---|---|
| 6,477,230 B1 | 11/2002 | Fuchs et al. |
| 7,500,783 B2 | 3/2009 | Kalender |
| 7,522,696 B2 | 4/2009 | Imai |
| 2003/0227999 A1 | 12/2003 | Cresens |
| 2006/0025672 A1 | 2/2006 | Sendai |
| 2008/0075225 A1 | 3/2008 | Kalender |
| 2009/0041191 A1* | 2/2009 | Suzuki ............. A61B 6/14 378/98.5 |
| 2009/0168966 A1* | 7/2009 | Suzuki ............. A61B 6/032 378/116 |
| 2012/0230473 A1* | 9/2012 | Stagnitto ......... A61B 6/4291 378/205 |

FOREIGN PATENT DOCUMENTS

| | | |
|---|---|---|
| CN | 101049243 A | 10/2007 |
| CN | 102274588 A | 12/2011 |
| CN | 203337825 U | 12/2013 |
| CN | 104320595 A | 1/2015 |
| DE | 19946736 C1 | 5/2001 |
| DE | 102007017979 A1 | 10/2007 |
| DE | 102006044783 A1 | 4/2008 |

* cited by examiner

*Primary Examiner* — Hoon Song
(74) *Attorney, Agent, or Firm* — Laurence Greenberg; Werner Stemer; Ralph Locher

(57) ABSTRACT

A radiography device and a radiography method are specifically adapted for examinations in the field of pediatric radiology. The radiography device examines a diagnosis-relevant region of a patient. The device has a radiation source, which emits radiological rays in an irradiation direction. An irradiation surface is selectable in dependence of a specified examination region of the patient. The radiography device also has a measurement field. The size of the measurement field is changeable such that the size of the measurement field and the size of the irradiation surface correlate.

17 Claims, 2 Drawing Sheets

RADIOGRAPHY DEVICE AND METHOD FOR EXAMINATIONS IN THE FIELD OF PEDIATRIC RADIOLOGY

CROSS-REFERENCE TO RELATED APPLICATION

This application claims the priority, under 35 U.S.C. §119, of German patent application DE 10 2013 205 499.8, filed Mar. 27, 2013; the prior application is herewith incorporated by reference in its entirety.

BACKGROUND OF THE INVENTION

Field of the Invention

The present invention lies in the field of pediatric radiology. A radiography device is a technical device for radiological imaging and/or therapy. It comprises at least an X-ray source and an X-ray detector and it can be based on analog or digital recording technology. The image processing of the captured signals can be based on various techniques (e.g. for a sectional image technique, filtered back projection, tomosynthesis etc.). For real-time transillumination, it is also possible to use X-ray image amplifiers as sensors or CCD elements.

SUMMARY OF THE INVENTION

It is the object of the present invention to provide a radiography device and a method with which a diagnosis-relevant region is optimally irradiated. The device and the method should preferably be adapted optimally for children or for pediatrics in terms of the measurement field, image quality and radiation dose. A particular object is to keep a radiation dose as low as possible, while ensuring the quality of the recording.

The achievement of the object with respect to the claimed radiography device will be described below. Features, advantages or alternative embodiments mentioned here are intended to also likewise apply to the method and vice versa. In other words, the claims in question, which are directed to the radiography device, can also be developed with the features which are described or claimed in connection with the method, and vice versa. The features in question with respect to the radiography device are here formed by the corresponding functional features of the method.

With the above and other objects in view there is provided, in accordance with the invention, a radiography device for examining a diagnosis-relevant region of a patient, comprising:

a radiation source configured to emit radiological rays in an irradiation direction;

a measurement field disposed to measure radiological radiation impinging on a surface thereof; and an irradiation surface that is selectable in dependence on a specified examination region of the patient;

wherein a size of said measurement field is changeable to correlate the size of said measurement field with a size of said irradiation surface.

According to one aspect of the invention, a radiography device for examining a diagnosis-relevant region of a patient is provided. The radiography device comprises a radiation source, which emits radiological rays in an irradiation direction, a measurement field, with which radiological radiation impinging on a surface of the measurement field is measured, and an irradiation surface, which is selectable in dependence on a specified examination region of the patient. The size of the measurement field is changeable such that the size of the measurement field and the size of the irradiation surface correlate. Here, preferably only the diagnosis-relevant proportions should be impinged upon by the radiation, such that advantageously the radiation dose for the patient can be reduced and the radiation exposure can also be reduced.

The term "irradiation direction" in which radiological rays, or beams, are emitted relates to the point-shaped central ray or the chief ray direction, in which the rays are emitted from the radiation source or the X-ray tube and guided onto the patient. Here, the central ray is located in the center of a beam cone. The central ray is preferably guided such that it impinges upon the diagnosis-relevant region as orthogonally as possible.

The term "irradiation surface" relates to a surface on which the transmitted radiological rays impinge such that an organ situated in front of or behind said surface of the human body is examined using X-rays.

The term "diagnosis-relevant region" of a patient relates to an anatomical region of the body which is to be examined so as to discover a disease or damage that is suspected to be present at that location.

The term "examination region" relates to an anatomical region of the human body which surrounds the diagnosis-relevant region. The examination region is preferably determined such that an anatomic assignment (position or orientation in the entire body of the patient) is possible—it is therefore larger than the diagnosis-relevant region. This is also based on the fact that a positive diagnosis is not always discovered with certainty exactly at the location where the cause of the disease is suspected. In addition, a patient cannot always be positioned exactly or kept still, as in the case of children. Additionally, the orientation of the organs to be examined can vary from patient to patient. It is therefore not possible to indicate the diagnosis-relevant region with absolute accuracy or certainty. What is important, however, is to have an anatomical assignment at all. The examination region should thus be selected to be a region which is derived from the diagnosis-relevant region with the mentioned deviations.

The measurement field relates to the active measurement surface, which is used to determine the radiation dose. If, for example, a measurement chamber is configured in the form of an ionization chamber, the size of the measurement field is predetermined by the unchangeable size of the ionization chamber. With the measurement field size unchanged, the quantity of the radiation can thus be ascertained over the entire region (of the measurement field). However, a measurement field can also be configured in the form of what is known as a flat panel detector, or a semiconductor detector, or in the form of another detector. For example, if the measurement field is configured in the form of a CCD sensor, it is even possible, in addition to ascertaining the dose, to capture image data or data for the X-ray recording. Flat panel detectors have the advantage that an evaluation can take place on the screen directly after (temporally) the X-ray recording. The surface of the examination region and the surface of the irradiation region can coincide here. Semiconductor or sandwich detectors thus ascertain the quantity and the quality of the irradiation over the entire region that is covered by the measurement field.

One core idea of the invention is that dose determination is more accurate, the better the measurement field or its active surface is matched to a predetermined irradiation surface. To this end, the measurement field is changeable in its size and the measurement field size is selectable. It is furthermore important that, if the selected measurement field and the irradiation surface do not have the same size, their size ratio is known. This is equivalent to it being known in which way the measurement field and the irradiation surface correlate. The selection of the measurement field can in this case support the correlation of the measurement field and the irradiation surface such that the dose can be determined accurately.

Correlating thus means that a conversion between an irradiation surface and the surface of the measurement field is known and thus a reliable result when calculating the dose is achieved.

One fundamental idea of the invention thus lies in the reduction of the radiation dose in X-ray recordings of infants and babies, while achieving constant or improved image quality. To this end, the measurement chamber comprises variable measurement fields. In X-ray recordings for adults, measurement chambers in the form of ionization chambers are used, which are hardly suitable for taking recordings of children on account of their size. The measurement chambers used are not changeable in terms of size and in part project far beyond the organ of the infant, when recording an X-ray image. Therefore, the results in calculating the dose in children and infants is largely imprecise.

According to the invention, by contrast, the measurement field is matched to a selectable irradiation surface. The irradiation surface to which the patient is exposed determines which region of the patient is X-rayed. Here, too, the radiation dose is reduced, if only, or mainly, that region which is relevant for an examination is captured. Therefore, the diagnosis-relevant region that is specified by a medical person should be determined first. The examination region is selected on the basis of said diagnosis-relevant region, which is selected such that all diagnosis-relevant regions can be captured with a high or very high probability. Deviations can occur on account of the size of the patient, the orientation of the organs, and furthermore because it is difficult to "fix" children in one location. The selection of the examination region for the patient then leads to the selection of the irradiation surface, which should be kept as small as possible. Finally, the irradiation surface serves as a basis for defining a measurement field such that the dose of the irradiation can therefore be determined with great accuracy. On the basis of the determination of the examination region for the patient, the measurement field can be determined (with respect to size and/or position) and, resulting therefrom, the irradiation surface. Both parameters or aspects, that is to say the irradiation surface and the measurement field, should be kept as small as possible so that the image quality is as high as possible and so the radiation exposure is as low as possible.

With the variability of the irradiation surface, the size of the measurement field should also be varied, with the result that a known correlation between the size of the irradiation surface and the size of the measurement field can be used. To this end, the exact ratio between the irradiation surface and the size of the measurement field is specified as a specified factor which is included in the calculation of the total dose. In any case, a total dose of the irradiation in X-ray recordings of children can then be determined more reliably if the measurement field size is matched to the irradiation surface. In addition, with a more reliable determinable total dose, the quality of the recordings itself can also be increased.

Shape and size of the measurement field and shape and size of the irradiation surface can be identical in this case, but do not have to be. A rectangular irradiation surface also has a definable ratio with respect to a circular measurement field shape, such that the overall radiation dose is also determinable in this case.

According to a further aspect, the orientation of the measurement field and/or the orientation of the irradiation surface is changeable such that the position of the measurement field and the position of the irradiation surface coincide.

Depending on the shape of the measurement field and the shape of the irradiation surface, it is possible to indicate a center point for said surfaces. If the respective center points of the measurement field and of the irradiation surface are identical, the surfaces are located on top of each other, and their positions coincide. One advantage of this is that the ascertainment of the dose is then simple because the ratio between the surfaces can be determined easily. If, however, the measurement field and the irradiation surface do not coincide, but merely overlap or do not touch at all, the determination of the dose thus becomes significantly more difficult.

According to a further aspect, the measurement field is circular. This type of surface is suitable for recording a large number of organs in children. It is additionally possible for the irradiation surface to be circular, such that, owing to the identical type of surface of the measurement field and of the irradiation surface, the total dose is determinable with even greater accuracy.

According to a further aspect, the measurement field has the same size as the irradiation surface.

The determination of a total dose of the irradiation could be simpler and more accurate, the better the shape and size of the measurement field coincide with the shape and size of the irradiation surface. In particular, the measurement field could have the same size as the irradiation surface. If they have an identical surface shape, the surfaces of the irradiation surface and of the measurement field can thus coincide completely, such that they have an identical size and an identical surface shape.

According to a further aspect, the radiography device comprises a measurement chamber which has the measurement field, wherein the measurement chamber is held interchangeably on a stand such that the measurement field is aligned orthogonally to the irradiation direction and can be moved perpendicularly to the irradiation direction.

The term "measurement chamber" designates a concrete apparatus which encloses the measurement field or surrounds the measurement field. In this meaning, the measurement chamber delimits the size of the measurement field. If the measurement chamber is attached to the stand in a suitable manner, the radiation dose can be determined with the active measurement field. In addition, the position of the measurement field can be changed such that the measurement field and the irradiation surface coincide. It is advantageous if the radiation emitted by the radiation source impinges perpendicularly on the measurement field, because in that case, no geometrical conversion owing to an oblique angle of incidence is necessary. The measurement chamber should be portable. "Portable" means that it can be used at different positions and/or integrated at different positions and/or in various devices. The measurement chamber is thus not just adapted for a specific device, it can also be removed therefrom. To this end, a corresponding measurement chamber holder is preferably provided.

In order that the measurement chamber can also be used in X-ray apparatuses that are designed for adults, the measurement chamber can be attached to the measurement chamber holder. The measurement chamber should in this case be portable such that it can be used at other work places (for example stand, patient bed, X-ray table). The measurement chamber thus represents a cost-effective solution. The measurement chamber holder is provided to implement interchangeability. The measurement chamber can in particular be held interchangeably such that it can be interchanged for another measurement chamber, such as for example a conventional measurement chamber designed for adults. In addition, the (children's) measurement chamber can be interchanged easily and used on other devices and apparatuses—and thus also at different locations in the hospital. The measurement chamber is preferably not designed to be integral with the X-ray device or the medical apparatus. On account of the interchangeability and the portability of the measurement chamber, it is also possible to increase the acceptance for the use of the children's measurement chamber. Owing to the variable measurement field size, the measurement chamber can also be used for the examination of adults.

According to a further aspect, the measurement chamber encloses a centering surface and an illuminated template, wherein the illuminated template is used to optically image a template image onto the centering surface.

The template indicates here the center point of the beam cone, such that optimum centering onto the diagnosis-relevant region is facilitated. The objective is for both a light ray field, or in other words the template image, and the X-ray field, or in other words the irradiation surface, to be identical or to be made to coincide. This happens by making the crosshairs and the center of the diagnosis-relevant region coincide.

Especially in X-ray recordings of children, one problem owing to the lack of devices (since only intended for adults) can be that of making the irradiation direction or the irradiation surface coincide with the measurement field. An image of the illuminated template is therefore generated on a centering surface, which is mounted fixedly to the measurement chamber or is part of the measurement chamber, using a template which is illuminated from behind. Said template image can comprise, in correspondence with the template, crosshairs and/or a circumferential border, such that the user can image the exact position of the irradiation surface onto the centering surface. A prerequisite for this is that the template is arranged in front of the light source such that the template image and the irradiation surface do not deviate from one another or deviate only to a very minor degree. The light source is frequently also referred to as a "dome lamp." In order to visualize the orientation of the measurement field, which is often concealed by the patient, a dome lamp is used, which is coupled to the measurement chamber and can visualize the extent or the size of the measurement field. To this end, the dome lamp can also be coupled (mechanically) to the measurement chamber. Before an X-ray measurement, the template can, for adjustment purposes, be pushed or folded in front of the dome lamp and into the beam path. The template and the dome lamp can subsequently be folded or pushed out of the beam path, before an X-ray recording takes place. In particular, the template can be selectable in dependence on the measurement field. Each measurement field size can in this case be assigned one specific template or one specific template size. In addition, a center point can be provided on the centering surface, with which the crosshairs projected by the template onto the centering surface and/or the circumferential border can be adjusted.

According to one further aspect, the size of the measurement field is selectable from 1 cm in diameter to 7 cm in diameter.

The size of the measurement field could be variable for example in steps of 1 cm and/or in a range between 1 cm and 7 cm in diameter. This means that the variable measurement field size should be between 1 cm and 7 cm, and should be adjustable in 1.0 cm steps. The term "diameter" in this case not only refers to a circular diameter. In an extended sense, it should also be understood as the diagonal of a rectangle or as the longest straight free path length of a surface having any desired shape or contour.

According to a further aspect, the radiography device comprises a detector, wherein the size of the measurement field is predetermined by the size of the active detector surface.

The detector can be used to immediately evaluate the recordings. The irradiation surface and the matching measurement field can additionally be changed or adapted immediately after a sample recording. To this end, the detector can supply image data to a screen, so that a user can determine whether the examination region was selected appropriately and whether the entire diagnosis-relevant region can be captured by the recording. The X-ray recordings are preferably recorded using a portable detector and are made to display on a monitor (screen). The system (based on the variable measurement field according to the invention) and/or the detector can in principle also be used in adult radiology. The irradiation surface and the measurement field can, however, also be strongly scaled down so that the dose is reduced.

The detector can be what is known as a semiconductor detector or a flat panel detector, wherein the detector can be constructed layer-wise from one or more semiconductor detectors with interposed filters. The flat panel detector can also be used to take image recordings or the X-ray recordings. The flat panel detector can be used for determining in particular the dose in the following manner: owing to a discrete construction of a matrix of photocells or other semiconductor sensors, the flat panel detector can be used to select a different size and shape for the measurement field. That is to say, such discrete regions of the array of photocells that are located inside a desired measurement field are selected. The same applies to CCD sensors or other semiconductor sensors. The values that can arise from the selection of said cells can then be used for the determination of the radiation dose. Furthermore, in a semiconductor detector, the absorption coefficient can be determined with the aid of an interposed filter. As a result, it is possible to derive or make a statement regarding the quality and quantity of the X-ray radiation.

The detector can be removed separately from the measurement chamber. The detector can additionally also be designed to be portable and can therefore be mounted, if needed, to a measurement chamber or a measurement chamber holder of another radiography device. Since the detector is not fixedly integrated in the X-ray system, but is portable, the efficiency of the system is increased, because it can be used in different work places.

As already mentioned, all further developments which have been described in connection with the X-ray device should also be understood to be further developments of the corresponding method.

With the above and other objects in view there is also provided, in accordance with the invention, a method for examining a diagnosis-relevant region of a patient with a radiography device, the radiography device having a measurement field for measuring radiological radiation impinging on a surface thereof, the method comprising the following method steps:

causing a radiation source to emit radiological rays in an irradiation direction;

selecting an irradiation surface in dependence on a specified examination region of the patient; and changing a size of the measurement field such that the size of the measurement field and a size of the irradiation surface correlate.

In other words, according to another aspect, a method for examining a diagnosis-relevant region of the patient using a radiography device is provided. Here, a measurement field is used, with which radiological radiation impinging on a surface of the measurement field is measured. The method comprises emitting radiological rays using a radiation source in an irradiation direction, selecting an irradiation surface in dependence on a specified examination region of a of the patient, and changing the size of the measurement field such that the size of the measurement field and the size of the irradiation surface correlate.

According to the method, the measurement field or the size of the measurement field is selected in dependence on the irradiation surface such that a known correlation between the surface of the measurement field and of the irradiation surface exists. Using the values from the measurement field, said known correlation can be used to ascertain the radiation dose on the irradiation surface, that is to say the total radiation dose which impinges on the patient in the case of a plurality of recordings. One advantage of the method is thus that it is possible to determine the radiation dose accurately even for small irradiation surfaces.

According to one aspect, the orientation of the measurement field and/or the orientation of the irradiation surface is changed such that the position of the measurement field and the position of the irradiation surface coincide.

According to one aspect, a sample measurement is carried out and the result of the sample measurement is included in a total dose calculation.

Carrying out a sample measurement can be useful in order to confirm the correct selection of the irradiation surface and of the measurement field. If it turns out that the size and/or orientation of the irradiation surface and/or of the measurement field were selected appropriately, there is still some radiation exposure on account of the sample measurement. The radiation exposure resulting from the sample measurement can be included in the total dose calculation. The calculation of the total dose is thus more accurate and offers a reliable basis for further diagnostic treatment of the patient.

According to one aspect, the size of the measurement field and/or the size of the irradiation surface are changed in dependence on the result of the sample measurement.

If it turns out that the selection of the irradiation surface and/or of the measurement field in respect of their size was wrong, it is possible, before the actual X-ray recording, to change or adapt the corresponding sizes of the measurement field and/or of the irradiation surface. As a result, the patient is protected against excessive and undesired radiation exposure, since repeat X-ray measurements are avoided.

According to one aspect, the orientation of the measurement field and/or the orientation of the irradiation surface is changed in dependence on the result of the sample measurement.

However, if the sample measurement indicates that the orientation of the irradiation surface and/or of the measurement field was not optimum, it is possible, before the actual X-ray recording, to change or adapt said orientations. Here, the irradiation direction can be changed or the X-ray radiation can be deflected in another known way (for example using shields) in order to change the orientation of the irradiation surface.

It is thus in principle possible to include any sample measurement in the total dose determination.

According to one aspect, the method comprises automatic activation of a template in dependence on the selection of an organ program and optical imaging of the activated template on a centering surface.

Automatic activation of the template in dependence on the selection of an organ to be examined can both reduce the number of erroneous operations and the total examination time. This can be particularly important when examining children and infants, with the result that the young patients experience a lower amount of stress and less fear on account of the unfamiliar surroundings and since they are, at least for a short period of time, separated from their parents or guardians.

The radiography device according to the invention can also be described thusly: the measurement chamber baseplate and a detector, which is attached thereto or held thereon, together form a type of measurement chamber which is suitable for digital recordings and for the instantaneous capturing of the irradiation or of the dose of radiation. The size of the measurement field can be matched or changed depending on which size is needed for the measurement field. The size of the measurement field is changed here such that the measurement field and the irradiation surface suitably correlate.

After a sample measurement, the irradiation surface and the measurement field can be changed, wherein the dose of the sample measurement is included in a total dose calculation. A sample measurement can be used to check the suitable examination region and the suitable irradiation surface. To this end, the image of the sample recording is displayed on a monitor and evaluated by a user. Alternatively, this recording can already be included in the determination of the total dose. This can be combined with a software-based measurement field (such as for example a histogram equalization). With approximately 10% of the total dose, the quality and quantity of the radiation is ascertained using the sample recording or the "sample burst." It is thus also possible for the limit value for the total dose in an X-ray recording to be observed even in a subsequent change of the irradiation surface and of the measurement fields. After a sample recording, the predefined measurement field size can be changed on a display and the default value for this recording can be overridden.

Once the X-ray recording is triggered in 1-point technique, the image data are transferred to the image system, where it is displayed on the monitor after image processing with predefined parameters. "1-point technique" in this case refers to an illumination technology, in which only the voltage (kV) of the X-ray radiation needs to be input by the user. The necessary current intensity and the time (the MAS product) are controlled via the measurement chamber/illumination automatics. For further simplification of the measurement chamber positioning, in the case of recordings in the lying position, a detector tunnel and a measurement field template, which is dependent on the respective recording (or SID) can be used. (SID here means "Source Image Receptor Distance"). The term "detector tunnel" refers to a housing in which an image receiver is introduced (in the form of a detector or an imaging plate).

Other features which are considered as characteristic for the invention are set forth in the appended claims.

Although the invention is illustrated and described herein as embodied in a radiography device and an examination method in pediatric radiology, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
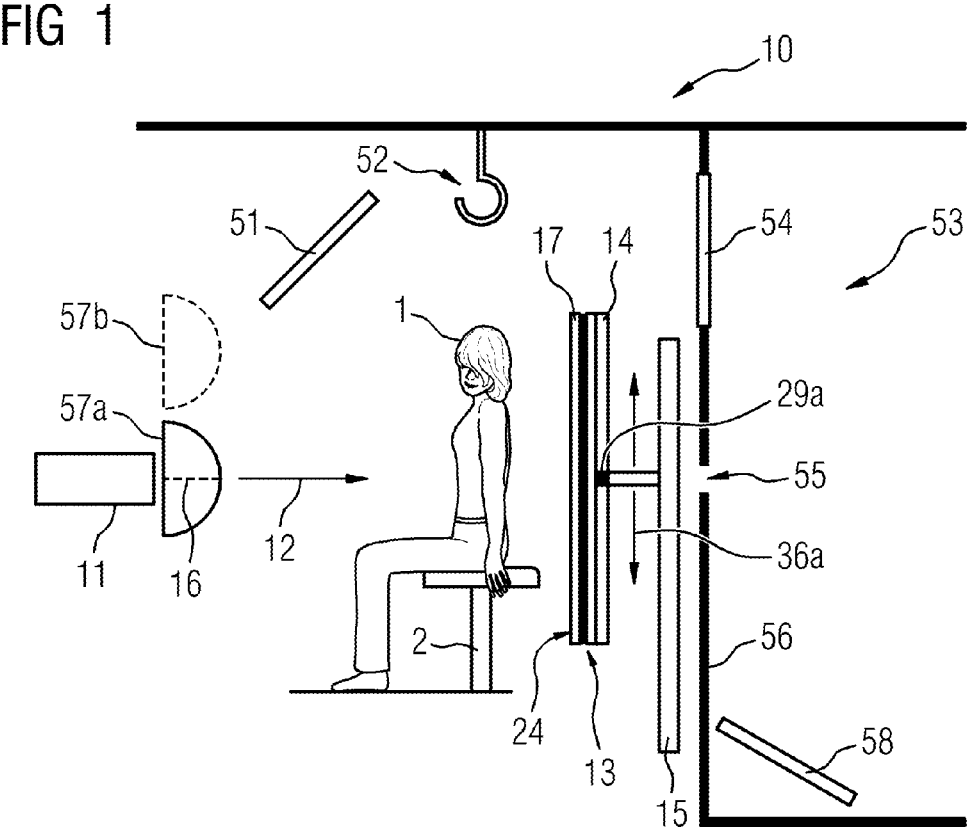
FIG. 1 is a schematic illustration of a radiography device according to the invention.

Referring now to the figures of the drawing in detail and first, particularly, to FIG. 1 thereof, there is shown a schematic illustration of a radiography device 10. A patient 1 is depicted, sitting on a chair 2. The patient 1 is located in the beam path and, in the irradiation direction 12, directly in front of a detector 17. The detector 17 is fixedly mounted to a measurement chamber holder 14. The detector 17 and the measurement chamber holder 14 together form the measurement chamber 13. The measurement chamber 13 is mounted, via its measurement chamber holder 14, to a stand 15, such that height adjustment or height displacement 36a of the measurement chamber 13 along the stand 15 is possible. Exact adjustment or centering of the measurement chamber 13 can occur through a center point 29a, which is marked on the front side of the detector 17. Any adjustment of the measurement chamber 13 must here be carried out in principle relative to the radiation source 11, which emits the radiological rays or X-rays in an irradiation direction 12. As a further aid in adjusting the radiation source 11 or in adjusting the measurement chamber 13, a dome lamp 57a can be arranged in front of the radiation source 11. Arranged in front of the dome lamp 57a, which is located in the beam path, is a template 16 which is arranged such that the measurement chamber 13 can be adjusted. It is important here that the radiation source 11 and the dome lamp 57a, which is arranged in front of it, with the template 16 have a mutually coordinated, that is to say identical, irradiation direction. The dome lamp 57a and the template 16 can be removed, moved or folded out of the beam path or the irradiation direction 12—illustrated at the alternative position 57b—once adjustment or centering has taken place. A rough centering of the measurement chamber 13 can be carried out using the dome lamp, while fine centering takes place using the SID-dependent template (SID—"Source Image Receptor Distance").

A holder 52 for supporting and orienting babies (also known as "Babix Holder") can be attached such that the baby is held in a specific orientation. A leaded window 54 is located in the radiation protection wall 56 of a control space 53 so that the patient 1 (that is to say the child or infant) can stay in contact with his or her guardian. Additional direct visual contact between the patient 1 and persons in the control space 53 is ensured with the use of a mirror 51 in the examination space.

In addition, a cutout 55 is provided in the radiation protection wall 56, which cutout 55 can be used to hold the patient 1 also during the X-ray recording. In addition, a foot switch 58 for triggering the X-ray recording is located in the control space 53, such that a single user can carry out all important actions.

Figure 2:
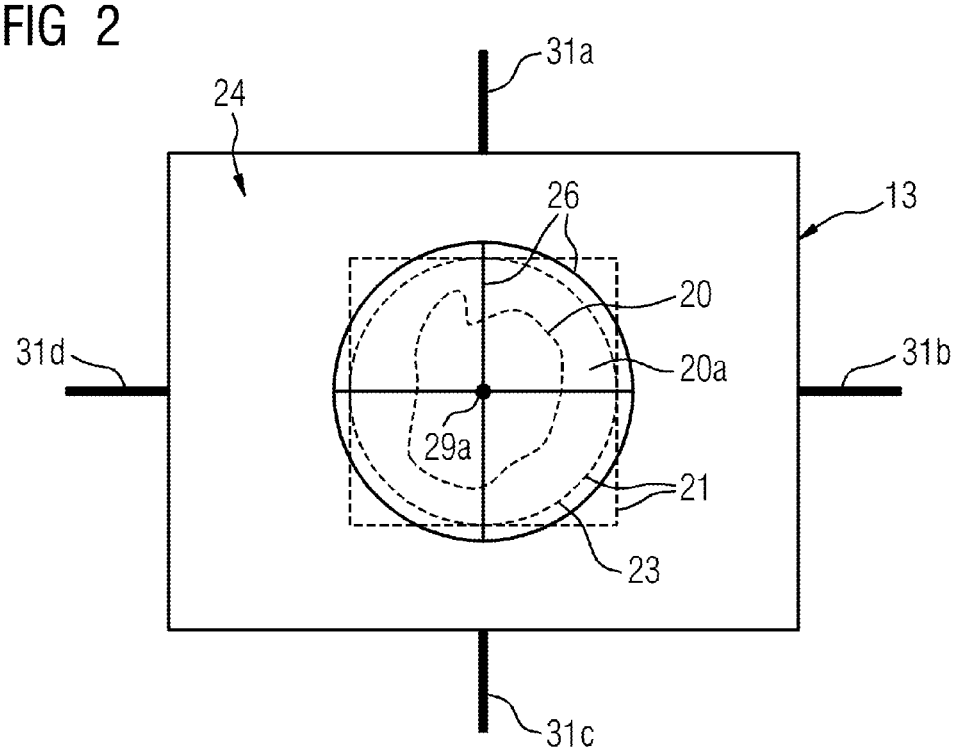
FIG. 2 is a schematic illustration of a centering surface having additional functional lines for clarification.

FIG. 2 depicts a schematic illustration of a centering surface 24. The centering surface 24 is located, viewed from the irradiation direction 12, on the front face of the measurement chamber 13. The centering surface 24 can thus also be located on the front face of the detector 17 (as indicated in FIG. 1). In order to move the measurement chamber 13 as already mentioned, handles (31a, 31b, 31c, 31d) can be attached to or mounted on the measurement chamber 13.

In FIG. 2, a diagnosis-relevant region 20 is shown having an irregular line profile. An examination region 20a surrounds the diagnosis-relevant region 20. In dependence on the examination region 20a, the irradiation surface 21 can be selected to be circular, rectangular, square or to have any other shape. The irradiation surface 21 is depicted in dashed lines so as to indicate that the irradiation surface 21 also cannot be seen directly on the centering surface 24 when taking a recording. In the ideal scenario, the irradiation surface 21 and the measurement field 23 (also indicated in the form of a dashed circle) are identical. The measurement field 23, which is located behind the centering surface 24 and represents a defined region of the detector (selection of photocells used), can likewise not be observed directly. For indicating the size of the measurement field 23, the template image 26 is visible on the centering surface 24 in the form of crosshairs, and optionally with a circumferential border. The template image 26 is generated by the template 16 and the light source located behind the template 16, for example the dome lamp 57a (cf. also FIG. 1). The template 16 can be made of a transparent thermoplastic, such as poly(methyl methacrylate), Perspex®, with the crosshairs being applied as a centering aid. The point of intersection of the crosshairs in this case represents the center point of the template. A center point 29a is depicted on the centering surface 24 such that the crosshairs of the template image 26 (or its lines of intersection) can be made to coincide with the center point 29a. It is thus possible to accurately center the measurement chamber 13.

Figure 3:
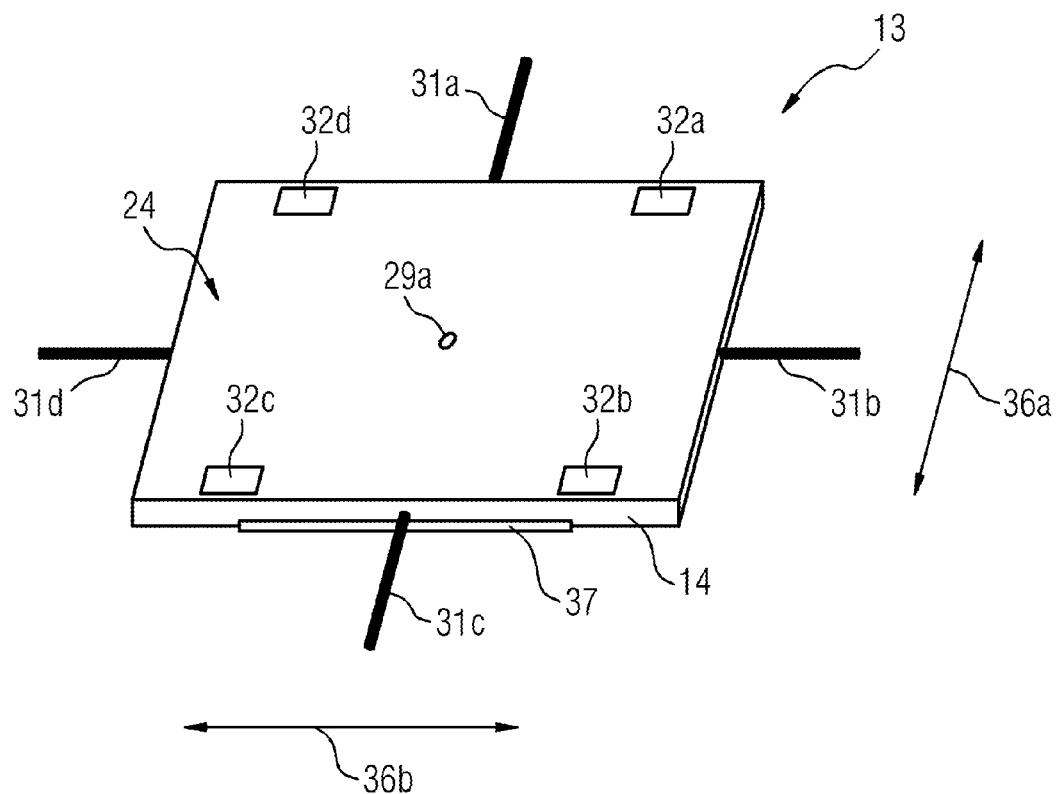
FIG. 3 shows a perspective view of a measurement chamber holder.

FIG. 3 shows a perspective view of the measurement chamber holder 14. The front side of the measurement chamber holder 14 can also serve as a centering surface 24, if a center point 29a is applied thereon. It should be noted that for this purpose the detector 17 must only be mounted after centering. The measurement chamber holder 14 has the handles 31a, 31b, 31c and 31d. Lateral displacement 36b is possible using the opposite handles 31a and 31c. The already mentioned height adjustment 36a is possible using the handles 31b and 31d, which are arranged perpendicularly to the first handle pair 31a and 31c. To this end, rails 37 can additionally be mounted on the measurement chamber holder 14. Alternatively, rails may also be part of the stand 15 so as to mount the measurement chamber holder 14 in a moveable fashion.

The measurement chamber holder 14 furthermore has devices for mounting the detector 17, which can take the form of holding clips 32a, 32b, 32c and 32d, for example.

Figure 4:
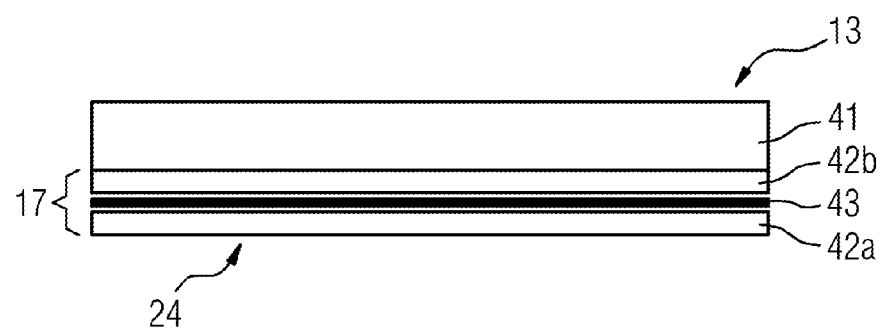
FIG. 4 shows a cross section of a measurement chamber.

FIG. 4 depicts a cross section of the measurement chamber 13, which is configured in this embodiment by a detector 17 or more precisely, as a layer detector or flat panel detector. The measurement chamber 13 furthermore has a baseplate 41, on which the detector 17 is held with the holding clips 32a, 32b, 32c and 32d (cf. FIG. 3). The detector 17 has, arranged in layers, a first semiconductor detector 42a, a second semiconductor detector 42b, and, located between the first semiconductor detector 42a and the second semiconductor detector 42b, a filter 43. The semiconductor detectors 42a and 42b can here be composed of photocells. The filter 43 can be used to additionally determine the absorption. The front face of the detector, that is to say the face which is facing towards the irradiation, can furthermore serve as a centering surface 24.

It should be noted in conclusion, that the description of the invention and the exemplary embodiments should in principle not be understood to be restrictive with respect to a specific tangible realization of the invention.

The invention claimed is:

1. A radiography device for examining a diagnosis-relevant region of a patient, comprising:
   a radiation source configured to emit radiological rays in an irradiation direction;
   a measurement field disposed to measure radiological radiation impinging on a surface thereof, said measurement field being a variable size measurement field configured to vary a size of an active surface thereof for measuring the radiological radiation; and
   an irradiation surface that is selectable in dependence on a specified examination region of the patient;
   wherein the size of said measurement field is changeable to correlate the size of said measurement field with a size of said irradiation surface;
   a measurement chamber enclosing said measurement field, said measurement chamber being displaceably held for movement orthogonally to an irradiation direction, said measurement chamber enclosing a centering surface; and
   a light source and an illuminated template configured to optically image a template image onto said centering surface, said template being disposed in front of said light source in a direction towards said measurement chamber and the template image substantially coinciding with said irradiation surface.

2. The radiography device according to claim 1, wherein a placement of at least one of said measurement field or said irradiation surface is changeable to cause a position of said measurement field and a position of said irradiation surface to coincide.

3. The radiography device according to claim 1, wherein said measurement field is a circular field.

4. The radiography device according to claim 1, wherein the size of said measurement field and the size of said irradiation surface are equal.

5. The radiography device according to claim 1, further comprising a measurement chamber enclosing said measurement field, and a support stand interchangeably holding said measurement chamber aligned orthogonally to an irradiation direction and displaceably in a plane perpendicular to the irradiation direction.

6. The radiography device according to claim 1, wherein the size of the measurement field is selectable between 1 cm and 7 cm in diameter.

7. The radiography device according to claim 1, comprising a detector having an active detector surface, wherein the size of said measurement field is determined by a size of said active detector surface.

8. A method for examining a diagnosis-relevant region of a patient with a radiography device, the radiography device having a measurement field for measuring radiological radiation impinging on a surface thereof, the method comprising the following method steps:
   causing a radiation source to emit radiological rays in an irradiation direction;
   selecting an irradiation surface in dependence on a specified examination region of the patient; and
   changing a size of the measurement field in accordance with the selected irradiation surface such that the size of the measurement field and a size of the irradiation surface correlate;
   providing a displaceable measurement chamber enclosing the measurement field and a centering surface, and selectively moving the measurement chamber orthogonally to an irradiation direction; and
   optically imaging a template image from a light source and an illuminated template onto the centering surface, with the template being disposed in front of the light source in a direction towards the measurement chamber and the template image substantially coinciding with the irradiation surface.

9. The method according to claim 8, which further comprises:
   changing at least one of an orientation of the measurement field or an orientation of the irradiation surface to cause a position of the measurement field and a position of the irradiation surface to coincide.

10. The method according to claim 8, which further comprises carrying out a sample measurement and including a result of the sample measurement in a total dose calculation.

11. The method according to claim 10, which further comprises changing at least one of a size of the measurement field or a size of the irradiation surface in dependence on the result of the sample measurement.

12. The method according to claim 10, which further comprises changing at least one of an orientation of the measurement field or an orientation of the irradiation surface in dependence on the result of the sample measurement.

13. The method according to claim 8, which further comprises automatically activating a template in dependence on a selection of an organ program and optically imaging the activated template on a centering surface.

14. The radiography device according to claim 1, wherein said measurement field is formed by a flat panel detector with a multiplicity of sensor cells, and said sensor cells are individually activatable so as to change the size of said measurement field.

15. The radiography device according to claim 14, wherein said sensor cells are semiconductor sensors.

16. The method according to according to claim 8, wherein the measurement field is formed by a flat panel detector with a multiplicity of sensor cells, and the step of changing the size of the measurement field comprises selectively switching individual sensor cells to an active state.

17. The radiography device according to claim 1, wherein said light source is a dome lamp.

* * * * *